(12) United States Patent
Sekharam

(10) Patent No.: US 12,194,144 B2
(45) Date of Patent: Jan. 14, 2025

(54) SOFT CHEWS WITH LOW WATER ACTIVITY AND METHODS OF MANUFACTURING SAME

(71) Applicant: FLORIDA RESEARCH GROUP LLC, Tampa, FL (US)

(72) Inventor: Kotha Sekharam, Tampa, FL (US)

(73) Assignee: Florida Research Group LLC, Tampa, FL (US)

( * ) Notice: Subject to any disclaimer, the term of this patent is extended or adjusted under 35 U.S.C. 154(b) by 70 days.

(21) Appl. No.: 16/577,007

(22) Filed: Sep. 20, 2019

(65) Prior Publication Data

US 2020/0093739 A1 Mar. 26, 2020

Related U.S. Application Data

(60) Provisional application No. 62/735,057, filed on Sep. 22, 2018.

(51) Int. Cl.
| | | |
|---|---|---|
| *A61K 9/00* | (2006.01) | |
| *A23L 27/20* | (2016.01) | |
| *A23L 33/115* | (2016.01) | |
| *A23L 33/125* | (2016.01) | |
| *A23L 33/135* | (2016.01) | |
| *A23L 33/14* | (2016.01) | |

(52) U.S. Cl.
CPC ............ *A61K 9/0056* (2013.01); *A23L 27/20* (2016.08); *A23L 33/115* (2016.08); *A23L 33/125* (2016.08); *A23L 33/135* (2016.08); *A23L 33/14* (2016.08)

(58) Field of Classification Search
None
See application file for complete search history.

(56) References Cited

U.S. PATENT DOCUMENTS

| | | | |
|---|---|---|---|
| 4,334,339 A * | 6/1982 | Holly ................... | A22C 7/0084 425/562 |
| 6,387,381 B2 | 5/2002 | Christensen | |
| 7,955,632 B2 | 6/2011 | Paulsen et al. | |
| 9,381,155 B2 | 7/2016 | Paulsen et al. | |
| 2006/0141009 A1* | 6/2006 | Huron ................... | A61P 33/14 426/635 |
| 2009/0280159 A1 | 11/2009 | Paulsen et al. | |
| 2011/0223234 A1 | 9/2011 | Paulsen et al. | |
| 2014/0141055 A1 | 5/2014 | Kluger et al. | |
| 2018/0169008 A1* | 6/2018 | Dixit ................... | A61K 31/496 |

FOREIGN PATENT DOCUMENTS

WO 2017106812 A1 6/2017

OTHER PUBLICATIONS

Waterman, K. C., et al., "Hydrolysis in pharmaceutical formulations." Pharmaceutical Development and Technology, May 2002, 7(2): Abstract.

* cited by examiner

*Primary Examiner* — Tigabu Kassa
(74) *Attorney, Agent, or Firm* — SALIWANCHIK, LLOYD & EISENSCHENK

(57) ABSTRACT

The invention pertains to methods of manufacturing soft chews containing highly heat-labile and moisture-labile active agents. The invention pertains to methods for manufacturing soft chew, comprising a) heating at a non-aqueous liquid carrier to a temperature of at least about 50° C., b) mixing the heated non-aqueous liquid carrier with at least one binding agent to form a uniform solution, c) mixing a solid excipient with the mixture produced in step b) to form a smooth dough, d) cooling the dough to about 30° C., e) mixing an active agent with the cooled dough, and f) forming soft chews from the dough produced in step e). The invention also pertains to soft chews manufactured by the methods of the invention. The soft chews produced according to these methods exhibit surprisingly higher stability of moisture-labile active agents while still providing desirable soft chew properties, such as soft moisture texture, taste, and palatability.

15 Claims, 1 Drawing Sheet

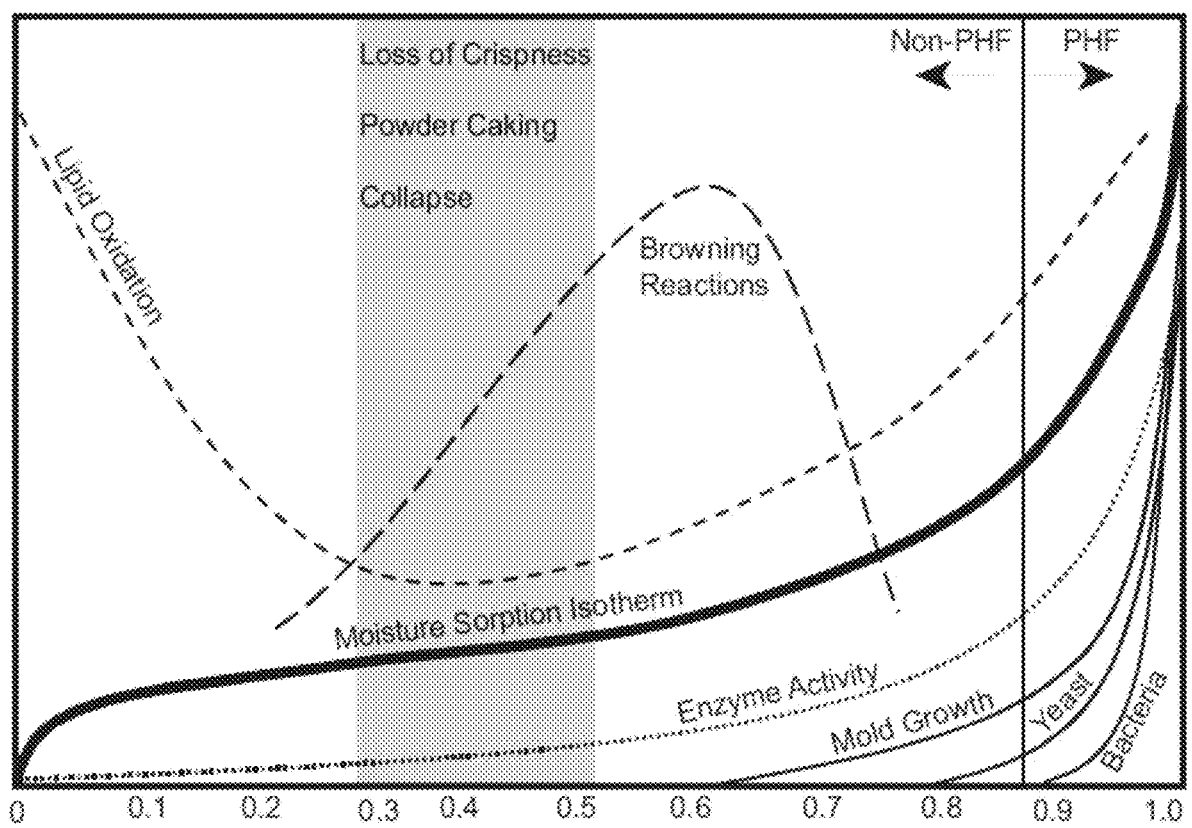

SOFT CHEWS WITH LOW WATER ACTIVITY AND METHODS OF MANUFACTURING SAME

CROSS REFERENCE TO A RELATED APPLICATION

This application claims the benefit of U.S. Provisional Application Ser. No. 62/735,057, filed Sep. 22, 2018, which is incorporated herein by reference in its entirety.

BACKGROUND OF THE INVENTION

Health supplements and oral medications are traditionally delivered as two solid dosage forms: oral tablets and oral capsules. Tablets can be made "chewable" by incorporating dry excipients for taste and flavor. Non-human animals, such as pet animals, prefer soft chews to dry tablets or capsules. Similarly, children and seniors also prefer tasty, non-chalky, and chewable tablets over a swallow tablet, capsule, or dry chewable tablet.

While chewable tablets are made by compressing dry ingredients, soft chews are made by making a "dough" with selective excipients, moistening agents and forming them to desired shape and weight, with chewable 'soft moist' texture. Certain examples of soft chews are disclosed in U.S. Pat. Nos. 7,955,632 and 9,381,155.

A variety of excipients are used to prepare dough for soft chews. Flours, including rice flour, wheat flour, potato flour, oat flour, and other substances, such as starches and dried yeast are combined with a desired active agent and mixed with moist binding agents, such as water, molasses or sugar syrups. Such dough can be shaped and formed into soft chews. Setting agents and gums can also be included in these formulations. The dough is extruded through a shaping die or deposited in a preformed cavity to form a chew of desired size and shape and cured to targeted hardness and consistency. Sometimes heat is also employed. Conventional soft chews have water-activity ($a_w$) higher than 0.6.

Certain moisture-labile and temperature labile active agents deteriorate due to the presence of 'available water' in the soft chews. For example, products with probiotics are normally available as tablets and dry powders. Probiotic are of several types. Most popular probiotics are the *Lactobacillus* bacteria and certain yeasts. Like other bacteria and yeasts, probiotics grow when water is available in the soft chew and it damages the quality of the soft chews. Therefore, most probiotics are not suitable for soft chew formulations.

Another example of a moisture-labile and temperature-labile ingredient is S-Adenosyl-L-methionine (SAMe). SAMe is physiological donor of methyl groups and is involved in enzyme transmethylation reactions. SAMe is used as a health supplement. Due to this nature, SAMe solid dosages are made with a protective coating and are packaged in an air tight film strip or container. Due to a high $a_w$ in existing formulations of soft chews, making a stable soft chew with stable SAMe is difficult.

Other active agents such as acetylsalicylic acid, omeprazole, amoxicillin, Co enzyme Q 10, and most enzymes are also moisture sensitive and cannot be included in soft chew formulations that have a high $a_w$. Certain pharmaceutical active ingredients like clavulanate are exceptionally difficult to formulate into a soft chew because of their moisture and heat sensitive properties.

Other examples of moisture sensitive drugs susceptible to hydrolysis, include esters (e.g., acetylsalicylic acid, and atropine); lactams (e.g., penicillin G); lactones (e.g., warfarin); acetals and hemi-acetals (e.g., erythromycin); carbamic esters (e.g., loratadine); imides (e.g., barbiturates); imines (e.g., diazepam); amides (e.g., chloramphenicol); alkyl halides (e.g., chlorambucil), ketals and hemi-ketals, or phosphates and sulfate esters. Certain such compounds are described by Waterman et al. (2002), Hydrolysis in Pharmaceutical Formulations, *Pharm. Dev. Tech.*, 7 (2), 113-146.

Active agents that require protection from moisture include: ACE inhibitors, including ramipril, benazepril, captopril, enalapril, lisinopril, fosinopril, perindopril, quinapril, moexipril and trandolapril; anti-convulsants, anti-hypertensive, drugs for Alzheimer's Disease, anti-depressants, antipsychotics, psychotherapeutics, diuretics, drugs for treating irritable bowel syndrome, anti-hyper lipidemic, osteo-regulatory, thrombolytics, and vasodilators.

Typically, to protect from moisture, these sensitive drug products are coated with polymers and are provided in solid dosage forms. The coating process is tedious and costly. Also, pharmaceutical doses in solid forms are not preferred for administration of active agents, particularly, to non-human animals.

Efforts have been made to reduce water content in soft chews; however, lowering water content in soft chews makes them dry, hard, brittle, and less palatable. Also, even a minimal quantity of water/moisture has negative effect on these moisture labile active agents.

U.S. Pat. No. 6,387,381 discloses an extrudate formed of a matrix having starch, sugar, fat, polyhydric alcohol, and water. The resulting soft chews have water-activity of about 0.60 to about 0.75.

U.S. Patent Publication No. 2016/067443 teaches a process for the manufacture of compressed soft chew tablets involving 2 lengthy steps, including granulation.

U.S. Pat. Nos. 7,955,632 and 9,381,155, and U.S. Patent Publication Nos. 2014/0141055, 2009/0280159, 2006/0141009, and 2011/0223234 teach methods of making soft chews.

U.S. Pat. Nos. 7,955,632 and 9,381,155 describe methods where an active agent is mixed with various inactive agents and PEG in a multi-step process where the temperature of the ingredients and mixtures in any step is not more than 10° C. above room temperature.

U.S. Patent Publication No. 2014/0141055 describes methods where an active agent is mixed with a liquid carrier (e.g., PEG) where the liquid carrier is heated until melted. The melting point of PEG is typically between 45° C. to 100° C. based on molecular weight. Therefore, in the methods described in this publication an active agent is heated to at least about 45° C. Such high temperature is not suitable for certain active agents like probiotic cultures or SAMe.

U.S. Patent Publication No. 2009/0280159 describes methods where an active agent is mixed with various inactive agents and a binding agent in a multi-step process where no extrusion, cooking, shearing, compression, or cooling step is performed and water or ingredients of animal origin are not added to the active agent or mixture.

U.S. Patent Publication No. 2006/0141009 describes methods of making soft chews having a moisture content of about 5.0 percent to about 7.5 percent and wherein the soft chew is formed by knockout, wherein the soft chew is not an extrudate.

U.S. Patent Publication No. 2011/0223234 describes methods where an active agent is mixed with various inactive agents and a non-aqueous fluid in a multi-step process where the temperature of the ingredients or mixtures in any step is not more than 10° C. above room temperature.

As such, the prior art discloses soft chews having a high water content that are not suitable for long term storage. The prior art also discloses methods of making soft chews that require exposing an active agent to elevated temperatures, such as about 45° C., which degrade the active agent. Further, the prior art discloses methods where the binding agent is mixed with the active agent at temperatures that are not much higher than room temperature and require quickly mixing an active agent with the binding agent. Such mixing is difficult because the mixture solidifies quickly and does not allow proper mixing of the ingredients. Therefore, these methods may produce soft chews with uneven distribution of the active agent.

Therefore, methods of manufacturing soft chews with low water-activity, good palatability, and ease of manufacture are required.

BRIEF SUMMARY OF THE INVENTION

The invention provides methods of manufacturing soft chews containing highly heat-labile and moisture-labile active agents. The methods of the invention do not expose the active agents to high temperature and produce soft chews with very low water-activity. For example, the invention provides methods of manufacturing highly palatable soft chews that exhibit an $a_w$ of about 0.6 or lower.

The soft chews manufactured by the methods of the invention exhibit surprisingly higher stability of moisture-labile active agents while still providing desirable soft chew properties, such as soft moisture texture, and palatability. Also, the methods of manufacturing soft chews of the invention can be easily practiced, particularly, on an industrial scale.

In certain embodiments, the invention provides methods for manufacturing soft chew, comprising a) heating at a non-aqueous liquid carrier to a temperature of at least about 50° C., b) mixing the heated non-aqueous liquid carrier with at least one binding agent to form a uniform solution, c) mixing a solid excipient with the mixture produced in step b) to form a smooth dough, d) cooling the dough to about 30° C., e) mixing an active agent with the cooled dough, and f) forming soft chews from the dough produced in step e).

Because the soft chews of the invention have an $a_w$ of about 0.6 or below, these soft chews are resistant to degradation by microorganisms, such as, bacteria and fungi. Therefore, in certain embodiments, the soft chews of the invention need no preservatives. Also, because the methods of manufacturing soft chews according to the invention do not require water, the soft chews can be free from water.

Further embodiments of the invention provide soft chews having an $a_w$ of about 0.6 or below.

Soft chews of the invention can be used to orally deliver an active agent to a subject. Accordingly, methods of orally delivering an active agent to a subject in the form of soft chews are also provided. In preferred embodiments, the active agents contained within the soft chews of the invention are heat-labile and degrade at a temperature of above 30° C.

BRIEF DESCRIPTION OF THE FIGURES

FIG. 1 shows a water-activity stability diagram.

DETAILED DESCRIPTION OF THE INVENTION

Soft chews having low $a_w$ are desirable. One conventional method of achieving soft chews with lower $a_w$ is to make the "available water" as "bound" and hence unavailable for biological purposes. $a_w$ can also be reduced by including into soft chews salts, sugars, and humectants. Salt, sugar, sorbitol, glycerol, and propylene glycol are some of the commonly used ingredients used to decrease $a_w$. Safety, adverse odors, adverse flavors, nutritional value, economy, ease of use, texture, and shaping of soft chews limit the use of the humectants, salts, and sugars in soft chew formulations. To avoid these drawbacks of conventional methods of reducing $a_w$, certain embodiments of the invention provide methods of manufacturing soft chew that exhibit $a_w$ of about 0.6 or below.

In certain embodiments, the invention provides methods for manufacturing soft chew, comprising a) heating at a non-aqueous liquid carrier to a temperature of at least about 50° C., b) mixing the heated non-aqueous liquid carrier with at least one binding agent to form a uniform solution, c) mixing a solid excipient with the mixture produced in step b) to form a smooth dough, d) cooling the dough to about 30° C., e) mixing an active agent with the cooled dough, and f) forming soft chews from the dough produced in step e). The $a_w$ of soft chews produced according to this method is about 0.6 or below.

In the methods of the invention, a non-aqueous liquid carrier is heated to a temperature of at least about: 50° C., 55° C., 60° C., 65° C., 70° C., 75° C., 80° C., 85° C., 90° C., 95° C., or 100° C. In preferred embodiments, a non-aqueous liquid carrier is heated to a temperature of about: 50° C., 55° C., 60° C., 65° C., 70° C., 75° C., 80° C., 85° C., 90° C., 95° C., or 100° C.

The non-aqueous liquid carriers suitable for the methods of the invention are liquid and provide cohesiveness to the dough. Examples of the non-aqueous liquid carriers include glycerin, liquid polyethylene glycol (PEG), vegetable oil, glycerol formal, propylene glycol, ethylene glycol, butyl glycol, castor oil, cottonseed oil, sesame oil, safflower oil, soybean oil, and corn oil. Combinations of one or more of these non-aqueous liquid carriers are also envisioned.

Glycerin is commercially available at 99.7% purity with very low moisture content. Therefore, glycerin is a preferred non-aqueous liquid carrier for use in the methods of the invention.

In the methods of manufacturing soft chews according to the subject invention, a non-aqueous liquid carrier is used from about 10 to about 30% w/w of the soft chew produced. In preferred embodiments, the amount of non-aqueous liquid carrier used in the methods of the invention is from 12% to 28%, from 14% to 26%, from 16% to 24%, from 18% to 22%, or about 20% w/w of the soft chew produced. In particularly preferred embodiments, the amount of non-aqueous liquid carrier used in the methods of the invention is about 10%, 11%, 12%, 13%, 14%, 15%, 16%, 17%, 18%, 19%, 20%, 21%, 22%, 23%, 24%, 25%, 26%, 27%, 28%, 29%, or 30% w/w of the soft chew produced.

In some embodiments, the methods of the invention comprise mixing the heated non-aqueous liquid carrier with at least one binding agent. The step of mixing a binding agent with the heated non-aqueous carrier is performed when the non-aqueous carrier is hot. The resulting mixture is then mixed till it forms a uniform solution. Mixing can be performed for about 1 to 10 minutes, particularly, for 2 to 9, 3 to 7, 4 to 6, or about 5 minutes. Mixing can be performed using a mixture or a blender. Other suitable methods of mixing are known in the art and such embodiments are within the purview of the invention.

Non-limiting examples of binding agents include hydrogenated castor oil, hydrogenated oil, hydrogenated vegetable oil, stearic acid, lauric acid, myristic acid, cetyl alcohol, glycerol monostearate, palmitic acid, capric acid, margaric acid, arachidic acid, behenic acid, lignoceric acid, cerotic acid, bees wax, gum arabic, PEG, and gelatin. Additional binding agents include spermaceti wax, carnuba wax, Japan wax, bay berry wax, flax wax, bees wax, yellow wax, shellac wax, sugar cane wax, glyceryl monostearate, glyceryl distearate, glyceryl tristearate, glyceryl dipalmitate, glyceryl tripalmitate, glyceryl monopalmitate, glyceryl palmitostearate, glyceryl dilaurate, glyceryl trilaurate, glyceryl monolaurate, glyceryl monomyristate, glyceryl dimyristate, glyceryl trimyristate, hydrogenated palm kernel oil, hydrogenated peanut oil, hydrogenated palm oil, hydrogenated rapeseed oil, hydrogenated rice bran oil, hydrogenated soy bean oil, hydrogenated sun flower oil, and hydrogenated cotton seed oil.

In preferred embodiments, the binding agent is PEG. Polyethylene glycol is available in different molecular weights, for example, ranging from 200 Da to 8000 Da. PEGs of different molecular weights exhibit different viscosities and physical properties. Typically, PEGs of higher molecular weights have decreased solubility in water and other hydrophilic solvents, decreased hygroscopicity and vapor pressure, and increased melting/freezing range and viscosity. In preferred embodiments, PEG used in the methods of the invention have a molecular weight between 1,000 Da to 8,000 Da.

Gelatin is another preferred binding agent. Gelatin is obtained by the partial hydrolysis of collagen derived from, for example, skin, white connective tissues, and bones of animals. Gelatin is nearly tasteless and odorless, is a vitreous, brittle solid that is faintly yellow in color. Gelatin is soluble in aqueous solutions of polyhydric alcohols such as glycerol and propylene glycol. Additional binding agents suitable for use in the instant methods include gum arabic and stearic acid.

Combinations of one or more binding agents listed herein are also envisioned for use in the methods of the invention.

In certain embodiments of the methods of manufacturing soft chews according to the subject invention, the binding agent used is about 0.5% to 10% w/w. In preferred embodiments, the binding agent used in the methods of the invention is about 1% to 9%, 2% to 8%, 3% to 7%, 4% to 6%, or about 5% w/w of the soft chew produced. In particularly preferred embodiments, the binding agent used in the methods of the invention is about 1%, 2%, 3%, 4%, 5%, 6%, 7%, 8%, 9%, or 10% w/w of the soft chew produced.

In certain embodiments, the methods of making soft chews comprise adding one or more solid excipients to the uniform solution of the heated non-aqueous liquid carrier and at least one binding agent. The resulting mixture is then mixed till it forms a smooth dough. Mixing can be performed for about 1 to 10 minutes, particularly, for 2 to 9, 3 to 7, 4 to 6, or about 5 minutes. Mixing can be performed using a mixture or a blender. Other suitable methods of mixing are known in the art and such embodiments are within the purview of the invention.

Solid excipients can be food or pharmaceutical grade. Solid excipients provide bulk and act as carriers for the active agent. In addition, these ingredients can provide taste, texture, and overall feel to the product.

Non-limiting examples of the solid excipients include brewers dried yeast, calcium carbonate, calcium phosphate, powdered liver, dried potato, pre-gelatinized starch, croscarmellose sodium, cellulose, starch, sodium starch glycolate, sugars, whey, dried cheese, and cereal flour. Combinations of one or more of these solid excipients are also envisioned. Additional ingredients suitable for use as a solid excipient are known in the art and such embodiments are within the purview of the invention.

In the methods of the invention, solid excipient can be used from about 10% to 50% w/w of the soft chew produced. In preferred embodiments, the solid excipient is used from about 15% to 45%, 20% to 40%, 25% to 35%, or about 30% w/w of the soft chew produced. In particularly preferred embodiments, the solid excipient used in the methods of the invention is about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% w/w of the soft chew produced.

In preferred embodiments, the smooth dough comprising a non-aqueous carrier, a binding agent, and a solid excipient is cooled to about 30° C. to 40° C. In particularly preferred embodiments, the smooth dough is cooled to about 30° C., 31° C., 32° C., 33° C., 34° C., 35° C., 36° C., 37° C., 38° C., 39° C., or 40° C.

In further embodiments, the methods of the invention comprise mixing an active agent with the cooled dough. The resulting mixture is then mixed till the active agent is uniformly distributed throughout the cooled dough. Mixing can be performed for about 1 to 10 minutes, particularly, for 2 to 9, 3 to 7, 4 to 6, or about 5 minutes. Mixing can be performed using a mixture or a blender. Other suitable methods of mixing are known in the art and such embodiments are within the purview of the invention.

In certain embodiments, the active agent is a pharmaceutical or nutraceutical agent. Active agent can also be a microbial culture, for example, a probiotic culture. In preferred embodiments, the active agent is heat-labile and is inactivated or degraded at a temperature of about 30° C. to 45° C., such as about: 30° C., 31° C., 32° C., 33° C., 34° C., 35° C., 36° C., 37° C., 38° C., 39° C., 40° C., 41° C., 42° C., 43° C., 44° C., or 45° C.

Non-limiting examples of the active agents include an analgesic, an anti-inflammatory, a mineral, a nutraceutical, an antibiotic, an antiviral, an endoparasiticide, an ectoparasiticide, an anthelmetic, an antifungal, a probiotic, a vitamin, a herb, and a combinations thereof.

Preferred active agents include: SAMe, Co enzyme Q-10, omega oils, fish oil, Perna canaliculus, palmitoylethanolamide, ivermectin, amoxicillin, carprofen, firocoxib, enrofloxacin, lindamycin, and acetyl alicylic acid.

A pharmaceutically acceptable salt of SAMe can be used, such as, SAMe para-toluene sulphonate, SAMe-1,4-butene disulphonate, SAMe sulphate, SAMe tosylate, SAMe phytate, or SAMe tosylate disulfate. S-Adenosyl-Methionine paratoluene sulphonate is preferred. In certain embodiments, SAMe or SAMe salts may be coated with an enteric coating.

Preferred probiotics include: *Lactobacillus acidophilus, Bifidobacterium thermophilum, B. longum, L. fermentum, L. casei, B. bifidum, E. faecium*, and *B. coagulans*.

Other active agents include: non-steroidal anti-inflammatory drugs (e.g, carprofen, flunixine meglumine, ketoprofen, ketoprofen methyl ester, naproxen, meloxicam, robenacoxib, and firocoxib), medetomidine, phenylbutazone, hydromorphone, anti-emetics (e.g., maropitant, and maropitant salts, dextromethorphan, diphenhydramine, 8-chlorotheophylline, cisapride, omeprazol, famotidine, metoclopramide, promethazine, dolasetron, ondansetron, granisetron, ketamine, lansoprasol, meclizine, and mirtazepine), antihistamines/antipyretics (e.g., acepromazine, clemastine fumarate, cyproheptadine, famotidine, loratadine, hydroxyzine, meclizine hydrochloride, apoquel, chlorpheniramine, and diphenhydramine), antiparasitics (e.g., macrocyclic lactones (ivermectin, abamectin, doramectin, emamectin, moxidectin, milbemycin, and milbemycin oxime), imidacloprid, emodepside, levamisole, pyrantel, pyrantel pamoate, isoxazolines (e.g., sarolaner, afoxolaner, lotilaner, and fluralaner), derquantel, anticoccidials, benzimidazoles (thiabendazole, mebendazole, fenbendazole, oxfendazole, and albendazole), antimicrobials (e.g., pleuromutilins, polymyxins, aminoglycosides, fluoroquinolones (e.g., danofloxacin, ciprofloxacin, norfloxacin, ofloxacin, and levofloxacin), macrolides (e.g., azithromycin, erythromycin, and telithromycin), lincosamides (e.g., clindamycin), aminoglycosides (e.g., amikacin, streptomycin, and tobramycin), sulfonamides (e.g., sulfadoxine, sulfamethizole, and sulfisoxazole), penicillins, beta-lactams, tetracyclines (e.g., doxycycline hyclate, and minocycline), aminopenicillins, cephalosporins ($1^{st}$-4th generations, e.g., simplicef, ceftiofur, and cefovecin), prednisolone, and methylprednisolone.

Combinations of one or more active agents are also envisioned. Additional active agents are known to a person of ordinary skill in the art and such embodiments are within the purview of the invention.

The amount of an active agent included in the soft chews produced according to the methods of the invention ranges from about 0.1% to about 25% w/w of the soft chew. A therapeutically effective amount of an active agent may vary depending upon the intended application, the subject, and the disease condition being treated, e.g., the weight and age of the subject, and the severity of the disease condition. These parameters can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

Optionally, soft chews of the invention may include additional ingredients commonly used in pharmaceutical compositions for humans and animal use. For example, flavoring agents such as molasses, carrot, apple, bacon, hickory flavor; coloring agents such as iron oxide, titanium dioxide, aluminum lakes, caramel, sweeteners such as sugar, dextrose, sodium saccharin, sucralose, preservatives such as parabens, propionate, sorbic acid, and antioxidants such as hydroxyanisole (BHA), and butylated hydroxytoluene (BHT), Tertiary-butyl hydroquinone (TBHQ) can also be added. These ingredients can be added in any of the several mixing steps in the methods of the invention discussed above.

Certain embodiments of the invention provide soft chews produced according to the methods of the invention. Soft chews produced according to the methods of the invention have $a_w$ of about 0.6 or below. The methods of the invention do not require addition of water and produce soft chews having $a_w$ of about 0.6 or below. Therefore, the soft chews of the invention can be free of water or preservatives.

In preferred embodiments, soft chews produced according to the methods of invention retain at least about 90% activity of the active agent at the end of the manufacturing process compared to the activity of the active agent added during the preparation of the soft chews. For example, assuming 100% retention of the activity of the active agent, if an amount of an active agent added during the preparation of soft chews would produce soft chews having 100 units of activity of the active agent per gm of soft chews, the soft chews produced according to the methods of the invention retain at least about 90 units of activity of the active agent per gm of soft chew at the end of the manufacturing process. In preferred embodiments, soft chews produced according to the methods of the invention retain at least about: 90%, 91%, 92%, 93%, 94%, 95%, 96%, 97%, 98%, or 99%, activity of the active agent at the end of the manufacturing process compared to the amount of active agent added in the preparation.

Certain embodiments of the invention provide soft chews having $a_w$ of 0.6 or lower. In some embodiments, the soft chews of the invention comprise at least one non-aqueous liquid carrier, at least one binding agent, at least one solid excipient, and at least one active agent. Various non-aqueous liquid carriers, binding agents, solid excipients, and active agents discussed above in connection with the methods of the invention are also applicable to the soft chews of the invention and such embodiments are envisioned.

Soft chews of the invention can be used to orally deliver an active agent to a subject. Accordingly, methods of orally delivering an active agent to a subject in the form of soft chews of the invention are also provided.

A subject can be a human or a non-human animal, preferably, a mammal. When the subject is a human, the subject is typically a child or a senior. When the subject is a non-human animal, the subject is a domestic pet, such as a dog or a cat. The subject can also be, for example, a horse, cow, pig, camel, or ferret.

Definitions

As used herein, the singular forms "a", "an" and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising."

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%). Where the term "about" is used to describe target temperatures or durations of time used in certain processes, the target temperatures of durations of time can be varied within a range 0-10% around the target value (X±10%).

The term "w/w" as used herein to describe an amount of an ingredient in the soft chews of the subject invention indicates that the corresponding ingredient is present in the specified weight ratio of the ingredient to the total weight of the soft chew. For example, PEG of 10% w/w indicates that the soft chews contain 1 gm of PEG per 10 gm of final soft chews product.

In the present disclosure, ranges are stated in shorthand, to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, and 0.7-1.0.

When ranges are used herein, such as for dose ranges, combinations and sub-combinations of ranges (e.g., sub-ranges within the disclosed range), specific embodiments therein are intended to be explicitly included.

Water activity ($a_w$) is defined as the ratio of the vapor pressure of water in a material to the vapor pressure of pure water at the same temperature. $a_w$, not the water content, determines the lower limit of available water for microbial growth. Water activity influences not only microbial spoilage but also chemical and enzymatic reactivity. Growth of most bacteria is inhibited at $a_w$ below about 0.9; most yeast cease growing at $a_w$ below 0.87; and mold cease growing at $a_w$ below 0.8. No microbial proliferation occurs at $a_w$ of 0.60 and particularly, below 0.60.

A "soft chew" as used herein refers to a pharmaceutical unit dose that is solid at room temperature and has a rubbery texture appropriate for mastication in the mouth. Soft chew is particularly suitable for administration of an active agent to a non-human animal, such as pets, because non-human animals do not prefer swallowing pills. Indeed, administering a solid pill to a non-human animal is difficult because of the resistance the non-human animal may provide to such administration. Non-human animals prefer eating a soft chew because the non-human animals can experience and enjoy flavor that can be incorporated in the soft chew. Such soft chews have a softness that is similar to a cooked ground meat petty.

For the purpose of this invention a heat-labile active agent is degraded or inactivated at a temperature of above 30° C., preferably above 35° C., and even more preferably, above 40° C.

For the purpose of this invention a moisture-labile active agent is degraded or inactivated at a water activity of above 0.6, preferably above 0.7, and even more preferably, above 0.8.

The methods and soft chews of the invention are exemplified by the following embodiments:

1. A method for manufacturing a soft chew, comprising:
    a) heating a non-aqueous liquid carrier to a temperature of at least about 50° C.,
    b) mixing the heated non-aqueous liquid carrier with at least one binding agent to form a uniform solution,
    c) mixing a solid excipient with the uniform solution produced in step b) to form a smooth dough,
    d) cooling the smooth produced in step c) to between 30° C. and 40° C., and
    e) mixing an active agent with the cooled dough produced in step d), and
    f) forming the soft chew from the dough produced in step e).

2. The method of embodiment 1, comprising heating the non-aqueous liquid carrier to a temperature of about: 50° C., 55° C., 60° C., 65° C., 70° C., 75° C., 80° C., 85° C., 90° C., 95° C., or 100° C.

3. The method of embodiment 1 or 2, wherein the non-aqueous liquid carrier is: glycerin, polyethylene glycol (PEG), vegetable oil, glycerol formal, propylene glycol, ethylene glycol, butyl glycol, castor oil, cottonseed oil, sesame oil, safflower oil, soybean oil, corn oil, or a combination thereof.

4. The method of any preceding embodiment, wherein the non-aqueous liquid carrier is about: 10%, 11%, 12%, 13%, 14%, 15%, 16%, 17%, 18%, 19%, 20%, 21%, 22%, 23%, 24%, 25%, 26%, 27%, 28%, 29%, or 30% w/w of the soft chew produced in step f).

5. The method any preceding embodiment, wherein the mixing in step b) is performed for about: 1, 2, 3, 4, 5, 6, 7, 8, 9, or 10 minutes.

6. The method any preceding embodiment, wherein the binding agents is: hydrogenated castor oil, hydrogenated oil, hydrogenated vegetable oil, stearic acid, lauric acid, myristic acid, cetyl alcohol, glycerol monostearate, palmitic acid, capric acid, margaric acid, arachidic acid, behenic acid, lignoceric acid, cerotic acid, bees wax, gum arabic, PEG, gelatin, spermaceti wax, carnuba wax, Japan wax, bay berry wax, flax wax, bees wax, yellow wax, shellac wax, sugar cane wax, glyceryl monostearate, glyceryl distearate, glyceryl tristearate, glyceryl dipalmitate, glyceryl tripalmitate, glyceryl monopalmitate, glyceryl palmitostearate, glyceryl dilaurate, glyceryl trilaurate, glyceryl monolaurate, glyceryl monomyristate, glyceryl dimyristate, glyceryl trimyristate, hydrogenated palm kernel oil, hydrogenated peanut oil, hydrogenated palm oil, hydrogenated rapeseed oil, hydrogenated rice bran oil, hydrogenated soy bean oil, hydrogenated sun flower oil, hydrogenated cotton seed oil, or a combination thereof.

7. The method any preceding embodiment, wherein the binding agent is about: 1%, 2%, 3%, 4%, 5%, 6%, 7%, 8%, 9%, or 10% w/w of the soft chew produced in step f).

8. The method any preceding embodiment, wherein the mixing in step c) is performed for about: 1, 2, 3, 4, 5, 6, 7, 8, 9, or 10 minutes.

9. The method any preceding embodiment, wherein the solid excipient is: dried yeast, calcium carbonate, calcium phosphate, powdered liver, dried potato, pre-gelatinized starch, croscarmellose sodium, cellulose, starch, sodium starch glycolate, sugars, whey, dried cheese, cereal flour, or a combination thereof.

10. The method any preceding embodiment, wherein the solid excipient is about: 15%, 16%, 17%, 18%, 19%/o, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% w/w of the soft chew produced in step f).

11. The method any preceding embodiment, comprising in step d) cooling the dough to about: 30° C., 31° C., 32° C., 33° C., 34° C., 35° C., 36° C., 37° C., 38° C., 39° C., or 40° C.

12. The method any preceding embodiment, wherein the mixing in step e) is performed for about: 1, 2, 3, 4, 5, 6, 7, 8, 9, or 10 minutes.

13. The method any preceding embodiment, wherein the active agent is heat-labile and/or moisture labile.

14. The method any preceding embodiment, wherein the active agent is: an analgesic, an anti-inflammatory, a mineral, a nutraceutical, an antibiotic, an antiviral, an endoparasiticide, an ectoparasiticide, an anthelmetic, an antifungal, a probiotic, a vitamin, a herb, or a combinations thereof.

15. The method any preceding embodiment, wherein the active agent is: SAMe, SAMe para-toluene sulphonate, SAMe-1,4-butene disulphonate, SAMe sulphate, SAMe tosylate, SAMe phytate, or SAMe tosylate disulfate, Co enzyme Q-10, ivermectin, amoxicillin, carprofen, firocoxib, enrofloxacin, lindamycin, acetyl alicylic acid, *Lactobacillus*

*acidophilus, Bifidobacterium thermophilum, B. longum, L. fermentum, L. casei, B. bifidum, E. faecium, B. coagulans*, non-steroidal anti-inflammatory drug, medetomidine, phenylbutazone, hydromorphone, anti-emetics, antihistamines/antipyretics, antiparasitics, antimicrobials, prednisolone, methylprednisolone, or a combination thereof.

16. The method any preceding embodiment, wherein the active agent is about 0.1% to about 25% w/w of the soft chew produced in step f).

17. The method any preceding embodiment, comprising further mixing a flavoring agent, a coloring agent, a sweetener, or an antioxidant in any one of steps a) to e).

18. A soft chew produced by any preceding embodiment.

19. A soft chew comprising a non-aqueous liquid carrier, a binding agent, a solid excipient, and an active agent, wherein the soft chow has water activity ($a_w$) of about 0.6 or below.

20. The soft chew of embodiment 19, wherein the soft chew is free of: water or a preservative.

21. The soft chews of embodiment 19 or 20, wherein the soft chew exhibits at least about 90% activity of the active agent compared to the activity of the active agent used in the preparation of the soft chew.

22. The soft chew of any of embodiments 19-21, wherein the non-aqueous liquid carrier is: glycerin, polyethylene glycol (PEG), vegetable oil, glycerol formal, propylene glycol, ethylene glycol, butyl glycol, castor oil, cottonseed oil, sesame oil, safflower oil, soybean oil, corn oil, or a combination thereof.

23. The soft chew of any of embodiments 19-22, wherein the non-aqueous liquid carrier is about: 10%, 11%, 12%, 13%, 14%, 15%, 16%, 17%, 18%, 19%, 20%, 21%, 22%, 23%, 24%, 25%, 26%, 27%, 28%, 29%, or 30%.

24. The soft chew of any of embodiments 19-23, wherein the binding agents is: hydrogenated castor oil, hydrogenated oil, hydrogenated vegetable oil, stearic acid, lauric acid, myristic acid, cetyl alcohol, glycerol monostearate, palmitic acid, capric acid, margaric acid, arachidic acid, behenic acid, lignoceric acid, cerotic acid, bees wax, gum arabic, PEG, gelatin, spermaceti wax, carnuba wax, Japan wax, bay berry wax, flax wax, bees wax, yellow wax, shellac wax, sugar cane wax, glyceryl monostearate, glyceryl distearate, glyceryl tristearate, glyceryl dipalmitate, glyceryl tripalmitate, glyceryl monopalmitate, glyceryl palmitostearate, glyceryl dilaurate, glyceryl trilaurate, glyceryl monolaurate, glyceryl monomyristate, glyceryl dimyristate, glyceryl trimyristate, hydrogenated palm kernel oil, hydrogenated peanut oil, hydrogenated palm oil, hydrogenated rapeseed oil, hydrogenated rice bran oil, hydrogenated soy bean oil, hydrogenated sun flower oil, hydrogenated cotton seed oil, or a combination thereof.

25. The soft chew of any of embodiments 19-24, wherein the binding agent is about: 1%, 2%, 3%, 4%, 5%, 6%, 7%, 8%, 9%, or 10% w/w.

26. The soft chew of any of embodiments 19-25, wherein the solid excipient is: dried yeast, calcium carbonate, calcium phosphate, powdered liver, dried potato, pre-gelatinized starch, croscarmellose sodium, cellulose, starch, sodium starch glycolate, sugars, whey, dried cheese, cereal flour, or a combination thereof.

27. The soft chew of any of embodiments 19-26, wherein the solid excipient is about: 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% w/w.

28. The soft chew of any of embodiments 19-27, wherein the active agent is heat-labile and/or moisture labile.

29. The soft chew of any of embodiments 19-28, wherein the active agent is: an analgesic, an anti-inflammatory, a mineral, a nutraceutical, an antibiotic, an antiviral, an endoparasiticide, an ectoparasiticide, an anthelmetic, an antifungal, a probiotic, a vitamin, a herb, or a combinations thereof.

30. The soft chew of any of embodiments 19-29, wherein the active agent is: SAMe, SAMe para-toluene sulphonate, SAMe-1,4-butene disulphonate, SAMe sulphate, SAMe tosylate, SAMe phytate, or SAMe tosylate disulfate, Co enzyme Q-10, ivermectin, amoxicillin, carprofen, firocoxib, enrofloxacin, lindamycin, acetyl alicylic acid, *Lactobacillus acidophilus, Bifidobacterium thermophilum, B. longum, L. fermentum, L. casei, B. bifidum, E. faecium, B. coagulans*, non-steroidal anti-inflammatory drug, medetomidine, phenylbutazone, hydromorphone, anti-emetics, antihistamines/antipyretics, antiparasitics, antimicrobials, prednisolone, methylprednisolone, or a combination thereof.

31. The soft chew of any of embodiments 19-30, wherein the active agent is about 0.1% to about 25% (w/w).

32. A method of delivering an active agent to a subject, comprising administering a soft chew of any of embodiments 19-31 to the subject.

33. The method of embodiment 32, wherein the subject is a human or a non-human animal.

34. The method of embodiment 33, wherein the human is a child or a senior.

35. The method of embodiment 33, wherein the non-human animal is a dog or a cat.

All patents, patent applications, provisional applications, and publications referred to or cited herein are incorporated by reference in their entirety, including all figures and tables, to the extent they are not inconsistent with the explicit teachings of this specification.

Following is an example which illustrates procedures for practicing the invention. This example should not be construed as limiting. All percentages are by weight and all solvent mixture proportions are by volume unless otherwise noted.

Example 1—Manufacturing a Soft Chew Containing a Probiotic

The final composition of the soft chew produced according to the methods described in this Example 1 is provided in Table 1 below:

TABLE 1

Composition of soft chew produced according to the methods of this Example 1

| Ingredient | % |
| --- | --- |
| Brewers dried yeast | 26.0 |
| Starch-1500 | 25.0 |
| Calcium carbonate | 10.0 |
| Salt | 2.0 |
| Flavor powder | 12.5 |
| Glycerin | 20 |
| Gum arabic | 0.5 |
| Gelatin | 1.0 |
| Probiotic culture powder (active agent) | 3.0 |

The formulation depicted in Example 1 can be prepared by heating glycerin to a temperature of about 60° C. temperature. Heated glycerin is then mixed with gum arabic and gelatin to form a uniform mixture. Solid excipients containing brewers dried yeast, starch-1500, calcium carbonate, salt, and powdered flavor in amounts described in Table 1 are then mixed with the mixture produced in the previous step. The resulting mixture is then blended till it forms smooth dough, typically, about five minutes. The dough is then cooled to about 30° C., and a probiotic culture powder is added to the cooled dough and blended till uniform dough is produced. Typically, this takes about 5 minutes of mixing.

The dough containing the probiotic is transferred to a forming machine at 30° C. to mold in to individual dosage soft chew units of desired. shape, size, and weight. The dough can also be shaped in an extruder, or formed in to a sheet and cut into pieces of desired size. Once formed, the soft chews can be packaged to protect from environmental conditions.

$a_w$ of soft chews prepared by the method described in this Example is about 0.30 and below. At this low water-activity, the soft chews with probiotics stay stable. Soft chews prepared by using the method described in Example 1 were evaluated for palatability and acceptability. These soft chews were found to be highly acceptable to animals and have good moist texture.

Example 2—Manufacturing a Soft Chew Containing Fish Oil

The final composition of the soft chew produced according to the methods described in this Example 2 is provided in Table 2 below:

TABLE 2

Composition of soft chew produced according to the methods of this Example 2

| Ingredient | % |
| --- | --- |
| Brewers dried yeast | 15.0 |
| Rice flour | 12.0 |
| Potato flour | 12.0 |
| Calcium carbonate | 10.0 |
| Fish oil concentrate | 10.0 |
| Potato starch | 10.0 |
| Flax seed meal | 10.0 |
| Glycerin | 9.0 |
| Vegetable oil | 5.0 |
| Lecithin | 3.0 |
| Gum arabic | 2.0 |
| Salt | 1.0 |
| Gelatin | 1.0 |

The formulation depicted in Example 2 can be prepared by heating glycerin to a temperature of about 60° C. Heated glycerin is then mixed with gum arabic and gelatin to form a uniform mixture. Solid excipients containing brewers dried yeast, rice flour, potato flour, calcium carbonate, potato starch, flax seed meal, and salt in amounts described in Table 2 are then mixed with the mixture produced in the previous step. The resulting mixture is then blended till it forms smooth dough, typically, about five minutes. The dough is then cooled to about 30° C., and fish oil is added to the cooled dough and blended till uniform dough is produced. Typically, this takes about 5 minutes of mixing.

The dough containing fish oil is transferred to a forming machine at 30° C. to mold in to individual dosage soft chew units of desired shape, size, and weight. The dough can also be shaped in an extruder, or formed in to a sheet and cut into pieces of desired size. Once formed, the soft chews can be packaged to protect from environmental conditions.

$a_w$ of soft chews prepared by the method described in this Example is about 0.50 and below. At this low water-activity, the soft chews with fish oil stay stable. Soft chews prepared by using the method described in Example 2 were evaluated for palatability and acceptability. These soft chews were found to be highly acceptable to animals and have good moist texture.

I claim:

1. A method for manufacturing a soft chew, wherein said method consists of:
   a) heating at least one non-aqueous liquid carrier to a temperature of at least about 50° C.;
   b) mixing the heated non-aqueous liquid carrier with at least one binding agent to form a uniform solution;
   c) mixing at least one solid excipient with the uniform solution produced in step b) to form a smooth dough;
   d) cooling the smooth dough produced in step c) to about 30° C. to about 40° C.;
   e) mixing at least one active agent with the cooled dough produced in step d);
   optionally, mixing a flavoring agent, a coloring agent, a sweetener, and/or an antioxidant in any one of steps a) to e); and
   f) forming the soft chew from the dough produced in step e) by molding, extrusion, or forming a sheet of the dough followed by cutting; wherein
   the at least one non-aqueous liquid carrier is about 10% to 30% w/w of said soft chew,
   the at least one binding agent is about 0.5% to 10% w/w of said soft chew,
   water is not added during the manufacture of said soft chew,
   the dough produced in step e) is suitable for molding, extrusion, and sheeting followed by cutting, and
   said soft chew exhibits a water activity (aw) value of about 0.6 or below.

2. The method of claim 1, wherein the heating step consists of heating the at least one non-aqueous liquid carrier to a temperature of about 50° C. to 100° C.

3. The method of claim 1, wherein the at least one non-aqueous liquid carrier is selected from the group consisting of: glycerin, polyethylene glycol (PEG), vegetable oil, glycerol formal, propylene glycol, ethylene glycol, butyl glycol, castor oil, cottonseed oil, sesame oil, safflower oil, soybean oil, corn oil, and combinations thereof.

4. The method of claim 1, wherein the mixing in step b) is performed for about 1 to 10 minutes.

5. The method of claim 1, wherein the at least one binding agent is selected from the group consisting of: hydrogenated castor oil, hydrogenated oil, hydrogenated vegetable oil, stearic acid, lauric acid, myristic acid, cetyl alcohol, glycerol monostearate, palmitic acid, capric acid, margaric acid, arachidic acid, behenic acid, lignoceric acid, cerotic acid, bees wax, gum arabic, PEG, gelatin, spermaceti wax, carnuba wax, Japan wax, bay berry wax, flax wax, bees wax, yellow wax, shellac wax, sugar cane wax, glyceryl monostearate, glyceryl distearate, glyceryl tristearate, glyceryl dipalmitate, glyceryl tripalmitate, glyceryl monopalmitate, glyceryl palmitostearate, glyceryl dilaurate, glyceryl trilaurate, glyceryl monolaurate, glyceryl monomyristate, glyceryl dimyristate, glyceryl trimyristate, hydrogenated palm kernel oil, hydrogenated peanut oil, hydrogenated palm oil, hydrogenated rapeseed oil, hydrogenated rice bran oil, hydrogenated soy bean oil, hydrogenated sun flower oil, hydrogenated cotton seed oil, and combinations thereof.

6. The method of claim 1, wherein the at least one binding agent is about 1% to 10% w/w of the soft chew.

7. The method of claim 1, wherein the mixing in step c) is performed for about 1 to 10 minutes.

8. The method of claim 1, wherein the at least one solid excipient is selected from the group consisting of: dried yeast, calcium carbonate, calcium phosphate, powdered liver, dried potato, pre-gelatinized starch, croscarmellose sodium, cellulose, starch, sodium starch glycolate, sugars, whey, dried cheese, cereal flour, and combinations thereof.

9. The method of claim 1, wherein the at least one solid excipient is about 15% to 50% w/w of the soft chew.

10. The method of claim 1, wherein the mixing in step e) is performed for about 1 to 10 minutes.

11. The method of claim 1, wherein the at least one active agent is heat-labile and/or moisture labile.

12. The method of claim 1, wherein the at least one active agent is selected from the group consisting of: an analgesic, an anti-inflammatory, a mineral, a nutraceutical, an antibiotic, an antiviral, an endoparasiticide, an ectoparasiticide, an anthelmetic, an antifungal, a probiotic, a vitamin, a herb, and combinations thereof.

13. The method of claim 1, wherein the at least one active agent is selected from the group consisting of: (S-adenosyl-L-methione) (SAMe), SAMe para-toluene sulphonate, SAMe-1,4-butene disulphonate, SAMe sulphate, SAMe tosylate, SAMe phytate, or SAMe tosylate disulfate, Co enzyme Q-10, fish oil, *Perna canaliculus*, palmitoyl ehanolamide (PEA), ivermectin, amoxicillin, carprofen, firocoxib, enrofloxacin, lindamycin, acetyl alicylic acid, *Lactobacillus acidophilus, Bifidobacterium thermophilum, B. longum, L. fermentum, L. casei, B. bifidum, E. faecium, B. coagulans*, non-steroidal anti-inflammatory drug, medetomidine, phenylbutazone, hydromorphone, anti-emetics, antihistamines/antipyretics, antiparasitics, antimicrobials, prednisolone, methylprednisolone, and combinations thereof.

14. The method of claim 1, wherein the at least one active agent is about 0.1% to about 25% w/w of the soft chew.

15. The method of claim 1, comprising further mixing a flavoring agent, a coloring agent, a sweetener, and/or an antioxidant in any one of steps a) to e).

* * * * *